United States Patent [19]

Ravella et al.

[11] Patent Number: 5,205,915
[45] Date of Patent: Apr. 27, 1993

[54] CONVERSION OF METHANE USING CONTINUOUS MICROWAVE RADIATION (OP-3690)

[75] Inventors: Alberto Ravella, Sarnia; William J. Murphy, Brights Grove, both of Canada

[73] Assignee: Exxon Research & Engineering Company, Florham Park, N.J.

[21] Appl. No.: 858,810

[22] Filed: Mar. 27, 1992

Related U.S. Application Data

[63] Continuation of Ser. No. 686,332, Apr. 16, 1991, abandoned, which is a continuation of Ser. No. 457,428, Dec. 27, 1989, abandoned.

[51] Int. Cl.$^5$ .............................................. C07C 1/00
[52] U.S. Cl. .......................... 204/157.15; 204/157.43; 204/170; 204/171
[58] Field of Search ............... 204/157.25, 157.6, 168, 204/170, 172; 208/106-107, 133, 142; 585/648, 953

[56] References Cited

U.S. PATENT DOCUMENTS

| | | | |
|---|---|---|---|
| 4,574,038 | 3/1986 | Wan | 204/157.15 |
| 4,721,828 | 1/1988 | Withers | 585/500 |
| 4,919,974 | 4/1990 | McCune et al. | 427/249 |
| 4,975,164 | 12/1990 | Ravella et al. | 204/156 |
| 5,015,349 | 5/1991 | Suib et al. | 204/168 |

OTHER PUBLICATIONS

Gasner et al., "Microwave and Conventional Pyrolysis of a Bituminous Coal," Chem. Abstr. 106:7281h (1987).

*Primary Examiner*—John Niebling
*Assistant Examiner*—C. Delacroix-Muirheid
*Attorney, Agent, or Firm*—John W. Ditsler; James H. Takemoto

[57] ABSTRACT

Methane can be effectively converted to acetylene, ethylene, and hydrogen by subjecting the methane to continuous microwave radiation in the presence of at least one plasma initiator that is capable of initiating an electric discharge in an electromagnetic field.

14 Claims, No Drawings

CONVERSION OF METHANE USING CONTINUOUS MICROWAVE RADIATION (OP-3690)

This is a Rule 60 Continuation of U.S. Ser. No. 686,332 filed Apr. 16, 1991, now abandoned which is based on a Rule 60 Continuation of 457,428 filed Dec. 27, 1989, now abandoned.

BACKGROUND OF THE INVENTION

1. Field of the Invention

This invention relates to a method for converting methane to higher molecular weight hydrocarbons and hydrogen using continuous microwave radiation.

2. Description of Related Art

Microwave energy has been used to convert methane to other hydrocarbons. For example, U.S. Pat. No. 4,574,038 discloses that methane can be converted to ethylene and hydrogen in a batch process at pressures of from 0.3 to 1 atmosphere by subjecting the methane to microwave radiation in the presence of a metal powder catalyst. Another example of methane conversion using microwave energy is U.S. Pat. No. 3,663,394.

However, neither patent suggests the particular methane conversion process described below.

SUMMARY OF THE INVENTION

This invention concerns the synthesis of higher molecular weight hydrocarbons and hydrogen from a methane source. More specifically, methane can be converted into higher molecular weight hydrocarbons (e.g. acetylene and ethylene) and hydrogen by irradiating the methane with continuous microwave radiation in the presence of at least one elongated plasma initiator that is capable of initiating an electric discharge in an electromagnetic field. In a preferred embodiment, molecular hydrogen will be present initially and the plasma initiator will comprise a plurality of elongated metal wire segments arranged in close proximity to one another.

DETAILED DESCRIPTION OF THE INVENTION

This invention requires the presence of methane, at least one elongated plasma initiator capable of initiating an electric discharge in an electromagnetic field, and a source of continuous microwave energy.

The methane may be pure or mixed with other hydrocarbons (e.g., as in natural gas). Non-hydrocarbons (e.g. $CO_2$, $H_2S$, $N_2$, etc.) may be present as well.

The plasma initiator may be essentially any material capable of accumulating an electric charge when placed in an electromagnetic field and then dissipating the charge (or initiating an electric discharge), for example, by ionizing a gas environment. This includes metal initiators, non-metal initiators (including semi-conductors), and composites of metal and non-metal initiators. As used herein, "composite" is meant to include mixtures (or combinations) of metals and non-metals. Examples of suitable metal initiators are tungsten, iron, nickel, copper, their alloys, or mixtures thereof. Preferred metal initiators are tungsten, iron, or mixtures thereof, with iron being particularly preferred. Examples of suitable non-metal initiators include carbon, alumina, manganese dioxide, magnetite, nickel oxide (e.g. NiO), iron oxide (e.g. $Fe_3O_4$), calcium aluminate, cobalt oxide, chromium nitride, iron sulfide (e.g. $FeS_2$, $Fe_{1-x}S$), copper sulfide (e.g. $CuS_2$), or mixtures thereof. Calcium aluminate, carbon, iron oxide, or their mixtures are preferred non-metal initiators, with carbon being particularly preferred. Silica is not a suitable non-metal initiator. However, silica composited with a metal initiator or another non-metal initiator would be a suitable plasma initiator.

Although methane conversion can be effected using only one plasma initiator, conversion is enhanced if more than one (e.g., 6 or more) plasma initiators are used. Preferably, a plurality of plasma initiators are used. Most preferably, the plasma initiator will comprise a plurality of metal wire segments. Each plasma initiator should be of at least a minimum length that is sufficient to initiate an electric discharge when placed in an electromagnetic field. However, the precise minimum length of each initiator may vary with the frequency of the microwave source as well as the geometry of the reaction zone and of the initiator.

If more than one plasma initiator is used, a minimum distance should be maintained between each initiator to facilitate dissipation of the electric charge. However, the minimum distance will vary depending upon the frequency of the microwave source. As an example, the minimum distance should be at least about 0.25 cm, preferably at least about 0.5 cm, for a frequency of 2.45 GHz.

The plasma initiators should be elongated, but may be formed, combined, or bent in any convenient shape (e.g., straight, helix, spiral, and the like). Preferably, the initiators should be formed such that there are points or sharp edges at the ends or on the surface of the initiators.

The plasma initiators may be stationary within the reaction zone or they may be in motion. The motion can result from the initiators being fluidized by a gas (e.g. the methane feedstock) or by other means (e.g. an external magnetic field gradient).

The frequency of the microwave source can vary broadly. Typically, the microwave energy will have a frequency of at least 0.3 GHz, with frequencies centered around 0.915, 2.45, 5.80, or 22.0 GHz being presently preferred in North America; particularly frequencies centered around 0.915, 2.45, or 5.80 GHz; especially frequencies centered around 0.915 or 2.45 GHz. The microwave energy used in this invention is continuous.

Molecular hydrogen should also be present in the reaction zone to maintain the activity of the plasma initiators for methane conversion. The amount of hydrogen in the reaction zone during conversion should be sufficient to maintain a mole ratio of methane to hydrogen greater than 1:1, preferably at least 1:1.5, more preferably at least 1:2, and most preferably at least 1:4. Although some methane conversion may occur at mole ratios of 1:1 or less, greater conversion will be obtained at higher mole ratios because hydrogen tends to reduce or inhibit the formation of carbonaceous deposits on the plasma initiators. While not wishing to be bound by any particular theory, it is believed that at lower mole ratios, greater amounts of carbonaceous deposits accumulate on the initiators and inhibit their ability to ionize the gas environment.

Although extraneous molecular hydrogen need not be added, if a sufficient amount of hydrogen is not present initially in the reaction zone, the initiators will deactivate until a sufficient amount of hydrogen is present (or has accumulated, for example, by recycling the hydrogen formed during conversion) to retard deactivation and maintain the mole ratio at a level that will stabilize the methane conversion at a particular level. This so-called induction period results in an initial loss of initiator activity and, hence, a lower level of methane conversion than if hydrogen had been present initially. To avoid this undesirable loss of conversion, it is preferred to add extraneous hydrogen to the reaction zone initially to minimize or prevent the initial loss of initiator activity and methane conversion. This extraneous hydrogen may be pure or in a mixture with other gases (e.g. as from a naphtha reformer) and may be added to the reaction zone separately or in mixture with the methane.

This invention can be practiced at any convenient temperature and pressure, including ambient conditions. However, the relative amounts of acetylene and ethylene formed will vary with pressure, with a greater amount of ethylene being formed at elevated pressures (i.e., pressures greater than atmospheric). In addition to acetylene and ethylene, this invention also contemplates the formation of aromatic compounds such as benzene, alkyl benzenes, xylenes, and the like.

This invention will be further understood by reference to the following Examples which are not intended to restrict the scope of the appended claims.

Example 1

Conversion of Methane

A methane/hydrogen mixture (1:4 mole ratio) flowing at 25 ml/minute (milliliters/minute) at atmospheric pressure was contacted with 0.37 g of a straight tungsten wire (approximately 0.76 mm in diameter and cut into about 47 mm lengths) in a reactor of a straight piece of quartz tubing, 7 mm in internal diameter. The part of the tube containing the wire was inserted in a WR430 microwave waveguide and positioned approximately one-quarter waveguide wavelength from a short circuit plate. The reactor was then irradiated with continuous microwave radiation centered at a 2.45 GHz frequency, with an average power of 16 watts. The methane conversion was calculated to be 65.2% using the following equation:

$$\genfrac{}{}{0pt}{}{\% \text{ Methane}}{\text{Conversion}} = \left[ 1 - \frac{\text{wt. \% methane in the products}}{\text{wt. \% methane in the feed}} \right] \times 100$$

After about 10 minutes, the primary hydrocarbon products formed were acetylene (an average of 31.0 wt %), ethylene (an average of 5.6 wt %). The product stream also contained 42.3 wt % hydrogen (versus 33.3 wt % in the mixture fed to the reactor), small amounts of ethane (0.25 wt %), and smaller amounts of higher hydrocarbons. The product stream contained 20.05 wt % methane (versus 66.6 wt % in the mixture fed to the reactor).

Example 2

Effect of Power and Flow Rate on Methane Conversion

Using the apparatus of Example 1, a methane/hydrogen mixture flowing at 250 ml/minute (50 ml/minute of methane and 200 ml/minute of hydrogen) was introduced into the reactor. The average microwave power was 19 watts. After about 40 minutes under these conditions, the reaction products contained 35.7 wt % hydrogen, 50.3 wt % methane, 1.6 wt % ethylene, 0.13 wt % ethane, 12.1 wt % acetylene, and smaller amounts of higher hydrocarbons. The methane conversion was calculated to be 21.8%.

This experiment was repeated except that the flow rate of the methane/hydrogen mixture into the reactor was 638 ml/minute (128 ml/minute of methane and 510 ml/minute of hydrogen) and the average microwave power was 52 watts. After about 5 minutes under these conditions, the reaction products contained 34.5 wt % hydrogen, 43.0 wt % methane, 1.9 wt % ethylene, 0.10 wt % ethane, 19.6 wt % acetylene, and smaller amounts of higher hydrocarbons. The methane conversion was calculated to be 34.4%.

A comparison of these data with the data in Example 1 show that an increase in flow rate causes a reduction in methane conversion, while an increase in microwave power causes an increase in methane conversion.

Example 3

Effect of Elevated Pressure on Product Distribution

Using the apparatus of Example 1, a methane/hydrogen mixture flowing at 115 ml/minute (23 ml/minute of methane and 92 ml/minute of hydrogen) at standard temperature and pressure was introduced into the reactor operating at a total pressure of 355 kPa absolute (or 36.5 psig). The average microwave power was 16 watts. After about 5 minutes under these conditions, the reaction products contained 55.8 wt % hydrogen, 26.5 wt % methane, 6.1 wt % ethylene, 0.73 wt % ethane, 10.9 wt % acetylene, and smaller amounts of higher hydrocarbons. The methane conversion and the weight ratio of acetylene to ethylene in the products were calculated to be 40.0% and 1.79, respectively.

This experiment was repeated except that the methane/hydrogen mixture, flowing at 270 ml/minute (54 ml/minute of methane and 216 ml/minute of hydrogen) STP, was introduced into the reactor at a total pressure of 694 kPa absolute (or 86 psig). The average microwave power was 23 watts. After about 5 minutes under these conditions, the reaction products contained 39.1 wt % hydrogen, 47.0 wt % methane, 7.9 wt % ethylene, 1.94 wt % ethane, 4.2 wt % acetylene, and smaller amounts of higher hydrocarbons. The methane conversion and weight ratio of acetylene to ethylene in the products was calculated to be 22.8% and 0.53, respectively.

The data in this example show that an increase in pressure affects the product distribution and, in particular, increases the yield of ethylene at the expense of the acetylene.

What is claimed is:

1. A method for converting methane to acetylene, ethylene, and hydrogen which comprises
   (a) introducing methane into a reaction zone that contains at least one elongated plasma initiator capable of initiating an electric discharge in an electromagnetic field, and
   (b) subjecting the methane and plasma initiator to continuous microwave radiation, thereby initiating an electric discharge, ionizing the methane in the reaction zone, and converting at least a portion of the methane to acetylene, ethylene, and hydrogen.

2. The method of claim 1 wherein the plasma initiator is a metal.

3. The method of claim 2 wherein the metal is tungsten, iron, nickel, copper, their alloys, or mixtures thereof.

4. The method of claim 3 wherein the metal is tungsten, iron, or mixtures thereof.

5. The method of claim 1 wherein the plasma initiator is a non-metal other than silica.

6. The method of claim 5 wherein the non-metal is calcium aluminate, carbon, iron oxide, or mixtures thereof.

7. The method of claim 1 wherein the plasma initiator is a composite of a metal initiator and a non-metal initiator.

8. A method for converting methane, to acetylene, ethylene, and hydrogen which comprises
   (a) introducing methane into a reaction zone which contains a plurality of metal wires capable of initiating an electric discharge in an electromagnetic field, and
   (b) subjecting the methane and metal wires to continuous microwave radiation having a frequency of at least 0.3 GHz, thereby initiating an electric discharge, ionizing the methane in the reaction zone, and converting at least a portion of the methane to acetylene, ethylene, and hydrogen, wherein the mole ratio of methane to hydrogen is greater than 1:1 during conversion.

9. The method of claim 8 wherein the metal is tungsten, iron, nickel, copper, their alloys, or mixtures thereof.

10. The method of claim 9 wherein the metal is tungsten, iron, or mixtures thereof.

11. The method of claim 8 wherein the mole ratio of methane to hydrogen is at least 1:2 during conversion.

12. The method of claim 11 wherein the mole ratio of methane to hydrogen is at least 1:4 during conversion.

13. The method of claim 8 wherein at least one aromatic compound is formed during methane conversion.

14. A method for converting methane to primarily ethylene and hydrogen which comprises
   (a) introducing methane into a reaction zone that contains at least one elongated plasma initiator capable of initiating an electric discharge in an electromagnetic field, and
   (b) subjecting the methane and plasma initiator to continuous microwave radiation, thereby initiating an electric discharge, ionizing the methane in the reaction zone, and converting at least a portion of the methane to primarily ethylene and hydrogen.

* * * * *